(12) United States Patent
Suzuki

(10) Patent No.: US 9,392,751 B2
(45) Date of Patent: Jul. 19, 2016

(54) METHOD FOR CULTIVATING PLANT

(71) Applicant: SHOWA DENKO K.K., Minato-ku, Tokyo (JP)

(72) Inventor: Hiroshi Suzuki, Tokyo (JP)

(73) Assignee: SHOWA DENKO K.K., Tokyo (JP)

( * ) Notice: Subject to any disclaimer, the term of this patent is extended or adjusted under 35 U.S.C. 154(b) by 196 days.

(21) Appl. No.: 14/170,844

(22) Filed: Feb. 3, 2014

(65) Prior Publication Data
US 2014/0215910 A1    Aug. 7, 2014

(30) Foreign Application Priority Data
Feb. 4, 2013   (JP) .................................. 2013-019714

(51) Int. Cl.
*A01G 7/04* (2006.01)
*A01H 3/02* (2006.01)
(52) U.S. Cl.
CPC . *A01G 7/045* (2013.01); *A01H 3/02* (2013.01)
(58) Field of Classification Search
CPC ............ A01G 7/00; A01G 7/04; A01G 7/045
USPC ............... 47/1.01 R, 62 R, 62 N, 1.3, 58.1 R, 47/58.1 LS, 58.1 SE, DIG. 6, 1.4
IPC ................................................ A01G 7/00, 7/04
See application file for complete search history.

(56) References Cited

U.S. PATENT DOCUMENTS

| 2003/0005626 | A1 | 1/2003 | Yoneda et al. | |
| 2010/0289411 | A1* | 11/2010 | Smits | A01G 7/045 315/113 |
| 2012/0247013 | A1 | 10/2012 | Sung | |
| 2013/0162147 | A1* | 6/2013 | Jiang | H05B 37/0218 315/154 |
| 2014/0165462 | A1* | 6/2014 | Shigyo | A01G 33/00 47/58.1 LS |
| 2015/0223402 | A1* | 8/2015 | Krijn | A01G 7/045 47/58.1 LS |

FOREIGN PATENT DOCUMENTS

| JP | 06-276858 A | 10/1994 |
| JP | 08-103167 A | 4/1996 |
| JP | 2005-052105 A | 3/2005 |
| JP | 2006-067948 A | 3/2006 |
| JP | 2008-142005 A | 6/2008 |
| JP | 2012-179009 A | 9/2012 |

OTHER PUBLICATIONS

Extended European Search Report, dated Jun. 23, 2014, issued by the European Patent Office, in counterpart Application No. 14153586.4.
Communication dated Oct. 7, 2014 from the Japanese Patent Office in counterpart Application No. 2013-019714.

* cited by examiner

*Primary Examiner* — Lisa Tsang
(74) *Attorney, Agent, or Firm* — Sughrue Mion, PLLC

(57) ABSTRACT

A plant-cultivating method is provided which comprises a red light irradiation step (A) and a blue light irradiation step (B), wherein the step (A) and the step (B) are independently carried out for a predetermined period of time under cultivation conditions such that the humidity in a cultivation atmosphere at the step (A) is higher than that at the step (B). Preferably the humidities in a cultivation atmosphere at the step (A) and the step (B) are in the ranges of 60%-90% and 40%-60%, respectively.

7 Claims, 2 Drawing Sheets

METHOD FOR CULTIVATING PLANT

BACKGROUND OF THE INVENTION (1) Field of the Invention

This invention relates to a method for cultivating a plant. More particularly it relates to a method for cultivating a plant while the plant is irradiated with an artificial light using a light-emitting lamp for plant cultivation whereby growth of the plant is promoted.

(2) Description of Related Art

Light-emitting technology has heretofore been adopted for growing seedlings or promoting growth of plants whereby a cultivation period of plants can be shortened and frequency of harvesting in the same farm can be increased. Plants can be grown to a large size within a predetermined period of time, and the crop yield can be enhanced.

As a plant cultivation technique utilizing artificial light irradiation, an illumination facility for irradiating a plant alternately with green light and white light has been proposed, for example, in patent document 1. In this illumination facility, plants are irradiated alternately with green light having a wavelength of 500 to 570 nm and white light having a wavelength of 300 to 800 nm whereby simulated day and night are created. Consequently the sugar translocation within plant bodies is smoothly effected and growth of plants is enhanced.

Another proposal has been proposed in patent document 2, which comprises an illumination lamp facility equipped with a light emitting diode (LED) for irradiating plants alternately or concurrently with blue light having a wavelength of 400-480 nm and red light having a wavelength of 620-700 nm to supply light energy for cultivation, growth, and tissue cultivation of plants. This illumination lamp facility is characterized as irradiating plants selectively with light having a wavelength corresponding to the light absorption peak of chlorophyll, i.e., in the vicinity of 450 nm and the vicinity of 660 nm whereby the plants are cultivated with an enhanced energy efficiency.

It is stipulated in patent document 2 that blue light and red light may be irradiated either concurrently or alternately (see patent document 2, claim 1). More specifically it is described in this patent document that single radiation of blue light, single radiation of red light and concurrent radiation of blue light and red light are compared with each other, and it was verified that the concurrent radiation of blue light and red light exhibited an enhanced effect on healthy growth of plants, which is similar to the growth achieved by sun light radiation, whereas the single radiation of blue light or red light brings about unhealthy growth such as spindling growth of plants (see patent document 2, paragraph [0011]).

It is further described in patent document 2 that blue light and red light are alternately irradiated by blinking by means of a blinking pattern at a high frequency of several megahertz or more (see patent document 2, paragraph [0006]). However, patent document 2 is silent on a method of alternately conducting a blue light irradiation step and a red light irradiation step, and thus growth promoting effects achieved by the alternate light irradiation method are not verified.

PRIOR ART DOCUMENTS

Patent Documents

Patent document 1: JP 1994-276858A
Patent document 2: JP 1996-103167A

To enhance the productivity in plant cultivation, a plant cultivation method utilizing artificial light irradiation, which is simple and easy, and exhibits enhanced energy effect and excellent growth promotion effect, is eagerly desired.

BRIEF SUMMARY OF THE INVENTION

A primary object of the present invention is to provide an improved method of cultivating a plant using an artificial light-irradiating facility, whereby the plant can be cultivated with more enhanced growth promotion effect.

The present inventors made extensive research for providing an improved method for cultivating a plant using an artificial light-irradiating facility with more enhanced growth promotion effect, and have found that a plant-cultivation method comprising a step (A) of irradiating a plant with a red light and a step (B) of irradiating the plant with a blue light, wherein the two steps (A) and (B) are independently carried out for a predetermined period of time, exhibits an enhanced growth promotion effect, and further found that the growth promotion effect varies depending upon the cultivation conditions, especially the humidity in a cultivation atmosphere. Based on this finding, the present invention has been completed.

In accordance with the present invention, there are provided the following plant-cultivating methods.

(1) A method of cultivating a plant comprising a step (A) of irradiating a plant with a red light and a step (B) of irradiating a plant with a blue light, wherein the red light irradiation step (A) and the blue light irradiation step (B) are independently carried out for a predetermined period of time under cultivation conditions such that the humidity in a cultivation atmosphere at the red light irradiation step (A) is higher than that at the blue light irradiation step (B).

(2) The method of cultivating a plant as mentioned above in (1), wherein the humidity in a cultivation atmosphere at the red light irradiation step (A) is in the range of 60% to 90% and the humidity in a cultivation atmosphere at the blue light irradiation step (B) is in the range of 40% to 60%.

(3) The method of cultivating a plant as mentioned above in (2), wherein the temperature in a cultivation atmosphere at the red light irradiation step (A) is in the range of 18° C. to 25° C. and the temperature in a cultivation atmosphere at the blue light irradiation step (B) is in the range of 18° C. to 25° C.

(4) The method of cultivating a plant as mentioned above in (1), wherein the cultivation atmosphere at the red light irradiation step (A) is maintained at a humidity higher than the humidity of the cultivation atmosphere at the blue light irradiation step (B) while an air stream is allowed to flow in the cultivation atmosphere at a flow rate in the range of 0.1 m/sec to 0.5 m/sec at the red light irradiation step (A) and at a flow rate in the range of 0.3 m/sec to 1 m/sec at the blue light irradiation step (B).

(5) The method of cultivating a plant as mentioned above in (1), wherein the red light-irradiation step (A) and the blue light irradiation step (B) are alternately and repeatedly carried out over a period of at least one hour for each irradiation time.

(6). The method of cultivating a plant according to (1), wherein the red light irradiation step (A) and the blue light irradiation step (B) are carried out using an illumination lamp facility having red light emitting elements and blue light emitting elements, both of which are capable of being independently operated, and the red light emitting elements and the blue light emitting elements exhibit a light emission intensity ratio of red light to blue light of at least 1:1 as expressed by a ratio of photosynthetic photon flux density of red light to blue light.

(7). The method of cultivating a plant according to (1), wherein the red light irradiation step (A) and the blue light irradiation step (B) are carried out using an illumination lamp facility having red light emitting elements and blue light emitting elements, both of which are capable of being independently operated, and the red light emitting elements and the blue light emitting elements exhibit a light emission intensity ratio of red light to blue light in the range of 2:1 to 9:1 as expressed by a ratio of photosynthetic photon flux density of red light to blue light.

By the term "plant(s)" as used in this specification, we mean plants in a broad sense which include leaf plants, fruit plants such as strawberry and tomato, grains such as rice and wheat, and algae. The plants further include phytoplankton such as green algae, and mosses.

By independently carrying out the red light irradiation step (A) and the blue light irradiation step (B), and further controlling the humidity in a cultivation atmosphere in the specific range in the plant-cultivation method comprising a red light irradiation step (A) and a blue light irradiation step (B) according to the present invention, the total amount of ascorbic acid which is a valuable vitamin, in the grown plant is increased.

DETAILED DESCRIPTION OF THE INVENTION

Figure 1:
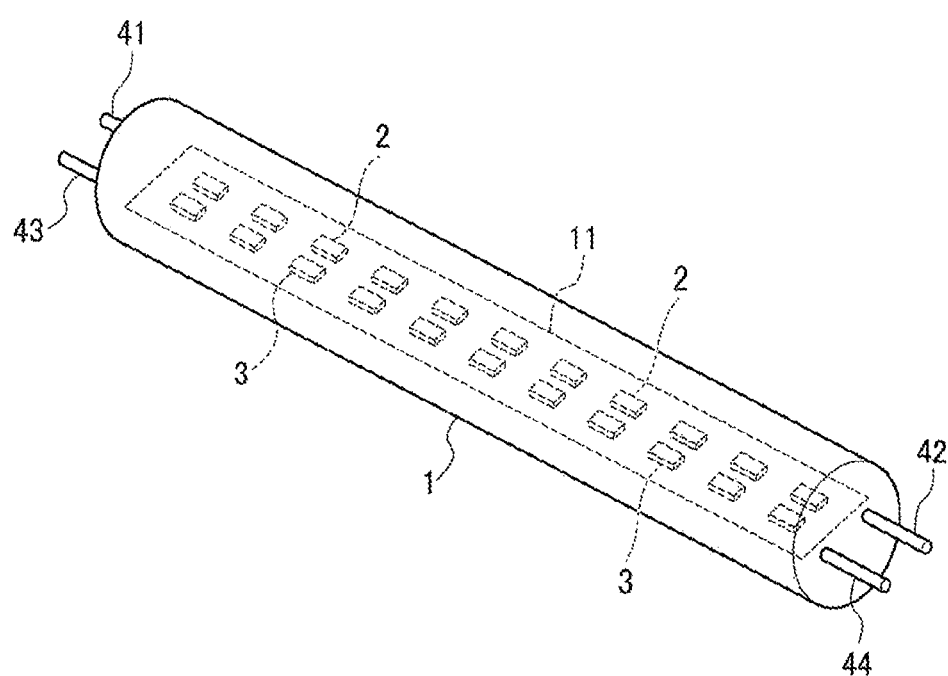
FIG. 1 is a perspective view of an example of an illumination lamp having red light emitting elements and blue light emitting elements as used in the plant-cultivation method of the present invention.

Preferred modes for practicing the invention will be described with reference to the accompanying drawings. The described modes by no means limit the scope of the invention.

The plant cultivation method of the present invention is characterized by comprising a step (A) of irradiating the plant with a red light and a step (B) of irradiating the plant with a blue light, wherein the red light irradiation step (A) and the blue light irradiation step (B) are independently carried out for a predetermined period of time under cultivation conditions such that the humidity in a cultivation atmosphere at the red light irradiation step (A) is higher than that at the blue light irradiation step (B).

When red light and blue light are irradiated on a plant, the light absorption curve of chlorophyll has different peaks attributed to the red light and the blue light. Thus the red light and the blue light exhibit different functions. The red light is concerned with activation of phytochrome, and blue light is concerned with activation of phototropin and cryptochrome.

The present inventors have investigated the difference between the functions of red light and blue light in the growth of plants, and found that red light tends to enlarge the area of plant leaves, and the blue light tends to enlarge the thickness of plant leaves and to be concerned with the production of vitamins. The present inventors have further investigated the functions of red light and blue light in the growth of plants, and found that, in the case when the humidity in a cultivation atmosphere at the red light irradiation step is higher than that at the blue light irradiation step, the content of ascorbic acid in the plant is increased.

Appropriate temperature and humidity are required for photosynthesis of plants. However, the desired temperature and humidity conditions vary depending upon the kind of light, i.e., whether the red light or the blue light is irradiated.

The growth promotion effect achieved by independently carrying out the red light irradiation step (A) and the blue light irradiation step (B) can be more enhanced when the temperature and the humidity in a cultivation atmosphere at the red light irradiation step (A) is maintained in the ranges of 18° C. to 25° C. and 60% to 90%, respectively; and the temperature and the humidity in a cultivation atmosphere at the blue light irradiation step (B) is maintained in the ranges of 18° C. to 25° C., and 40% to 60%, respectively.

The reason for which the above-mentioned enhancement in the growth promotion effect is not clear, but it is presumed that, when the red light irradiation step (A) and the blue light irradiation step (B) are independently carried out, the reaction of chlorophyll greatly varies depending upon the particular humidity in a cultivation atmosphere. In other words, adequate control of humidity in the cultivation atmosphere and independently taking steps of red light irradiation and blue light irradiation enhance the plant growth promotion effect. It is further presumed that the light irradiation conditions and the humidity change in a cultivation atmosphere have a close relationship with transpiration through stoma openings of plants and have an effect on the chemical reactions occurring inside the leaves.

It is preferable that the cultivation atmosphere at the red light irradiation step (A) is maintained at a humidity higher than the humidity of the cultivation atmosphere at the blue light irradiation step (B) while an air stream is allowed to flow in the cultivation atmosphere at a flow rate in the range of 0.3 m/sec to 1 m/sec at the blue light irradiation step (B) and at a flow rate in the range of 0.1 m/sec to 0.5 m/sec at the red light irradiation step (A). By allowing an air stream to flow at the above-mentioned flow rate, the humidity having an effect on plants can be adjusted adequately and uniformly within a short period of time, and the photosynthesis process of chlorophyll proceeds smoothly.

Illumination Lamp for Plant Cultivation

In the plant cultivating method of the present invention, an illumination lamp facility for plant cultivation having red light emitting elements and blue light emitting elements, both of which are capable of being independently operated, is preferably used for alternately and repeatedly carrying out the red light irradiation step (A) and the blue light irradiation step (B) over a predetermined period of time.

The illumination lamp facility is preferably provided with a control part capable of independently turning on and out the red light emitting elements and the blue light emitting elements. By the provision of the control part, the red light and the blue light can be irradiated alternately or concurrently, and for a desired period of time, depending upon the particular plant so as to attain the enhanced growth promotion effect.

The control part is preferably provided with a lamp controller (i.e., light emission intensity-controlling means) capable of controlling the light emission intensity ratio of red light to blue light. By the provision of the lamp controller, the light emission intensity ratio of red light to blue light can be controlled so as to attain more enhanced growth promotion effect.

FIG. 1 is a perspective view of a preferable example of an illumination lamp for plant cultivation which has red light emitting elements and blue light emitting elements. This illumination lamp 1 has a light irradiation part 11 having a rectangular shape in the planar view, and further has a control part (not shown) for controlling the light irradiation part 11.

As illustrated in FIG. 1, the light irradiation part 11 is provided with plural red light emitting elements 2 and plural blue light emitting elements 3. In the plant cultivation lamp 1, as exemplified in FIG. 1, the ratio in number of red light emitting elements 2 to blue light emitting elements 3 is 2:1.

Plural red light emitting elements 2 are arranged with equal intervals along a straight line extending in the length direction, and plural blue light emitting elements 3 are also arranged in a similar manner. The straight line of red light emitting elements 2 and the straight line of blue light emitting elements 3 are substantially parallel to each other.

The number of red light emitting elements 2 and the number of blue light emitting elements 3 may be the same or different in the illumination lamp 1, although the ratio in number of red light emitting elements to blue light emitting elements in the lamp illustrated in FIG. 1 is 2:1.

The rate of plant growth sometimes varies depending upon the light emission intensity ratio between blue light and red light. For example, some plants exhibit enhanced rate of growth when the red light emission intensity is larger than the blue light emission intensity. For these plants, it is preferable to use a plant cultivating illumination lamp 1 having a light emitting part provided with a larger number of red light emitting elements 2 than blue light emitting elements 3. By using the lamp 1 provided with a larger number of red light emitting elements 2 than blue light emitting elements 3, the light emission intensity of red light can be higher than that of blue light.

For some plants, the light emission intensity of red light is preferably larger than that of blue light. Practically, for these plants, the light emission intensity ratio of red light to blue light is preferably at least 1:1, more preferably in the range of 2:1 to 9:1, and especially preferably in the range of 2:1 to 5:1. It is preferable to use an illumination lamp having a light emitting part provided with a larger number of red light emitting elements than blue light emitting elements, which part gives output beam having a light emission intensity ratio in the above-mentioned range when an appropriate current is applied to the respective red light emitting elements and blue light emitting elements. The illumination lamp is preferably such that an applied electrical current can be exactly adjusted and the ratio of light emission intensity of red light to that of blue light can be desirably varied depending upon the particular kind of plant by precisely adjusting the electrical current.

If the ratio of light emission intensity of red light to that of blue light is smaller than the above-specified range, i.e., the blue light emission intensity is too large as compared with the red light emission intensity, the desired rate of growth is difficult or impossible to attain. In contrast, if the ratio of red light emission intensity to blue light emission intensity is larger than the above-specified range, i.e., the red light emission intensity is too large, the desired rate of plant growth is also difficult or impossible to attain, and, for example, undesirable growth such as spindly growth or overgrowth tends to occur.

As modification of the light irradiation part 11 of lamp 1 as illustrated in FIG. 1, which is provided with different numbers of red light emitting elements 2 and blue light emitting elements 3, various light emitting parts having red light emitting elements 2 and blue light emitting elements 3, which are arranged in different manners, can be used. Specific examples of the arrangement of red light emitting elements 2 and blue light emitting elements 3 in the light irradiation part 11 are illustrated in FIG. 2, (a) through (d).

Figure 2:
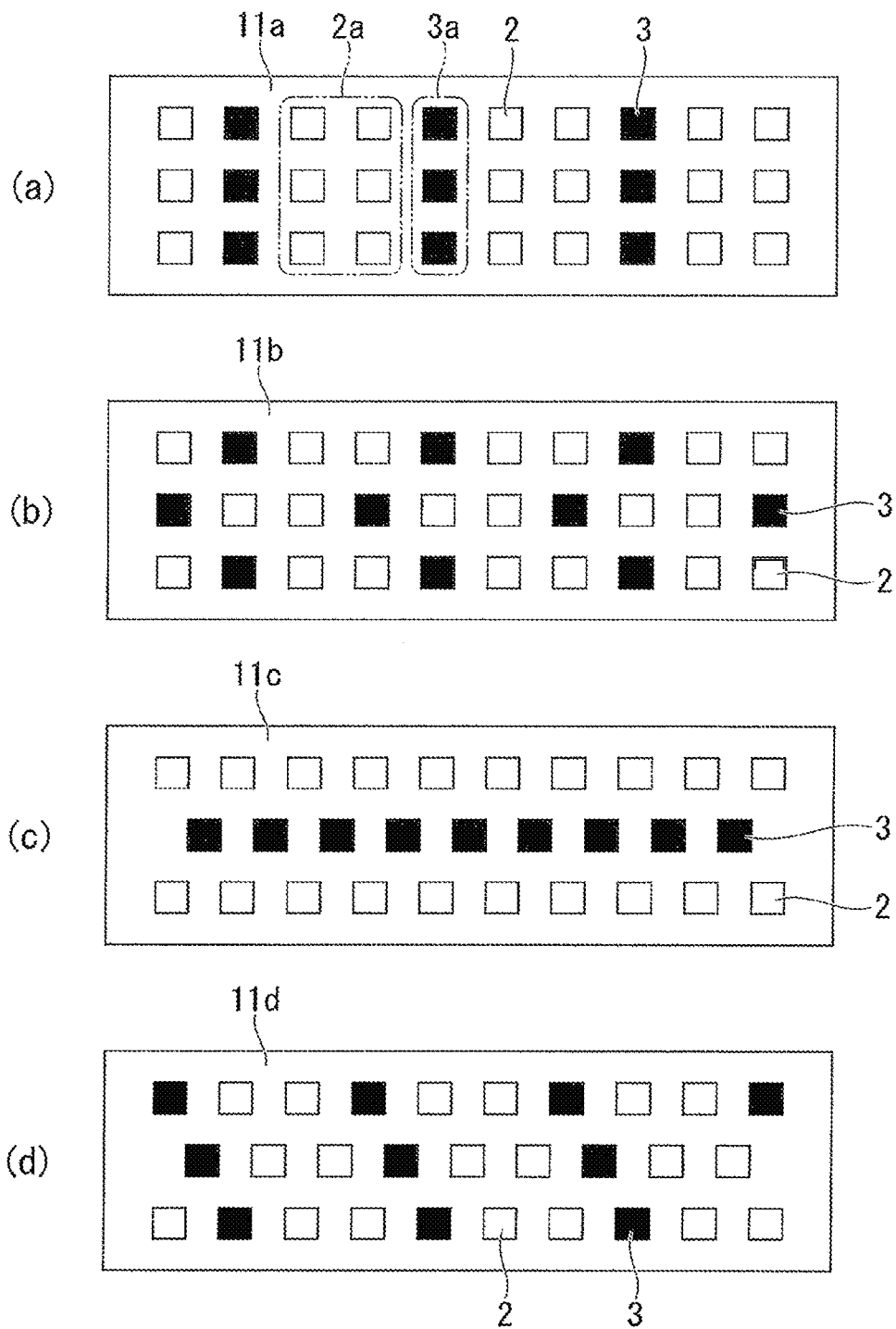
FIG. 2, (a) through (b) are schematic plan views showing arrangements of red light emitting elements and blue light emitting elements in illumination lamps as used in the plant-cultivation method of the present invention, wherein the arrangements of light emitting elements are different from those in FIG. 1.

In FIG. 2, (a) through (d), each of light emitting parts 11a, 11b, 11c and 11d have red light emitting elements 2 and blue light emitting elements 3, the ratio in number of the elements 2 to the elements 3 is 2:1. In these figures, white square □ and black square ■ indicate red light emitting element 2 and blue light emitting element 3, respectively. The red light emitting elements 2 and the blue light emitting elements 3 are preferably arranged so that the distribution of light emission intensity is uniform over the entire light emission surface of each part 11a, 11b, 11c or 11d.

In the light irradiation part 11a as illustrated in FIG. 2 (a), light emitting elements 2 and 3 are regularly distributed to form plural rows each extending in parallel in the longitudinal direction of the light irradiation part 11a, and form plural columns each extending in parallel in the direction perpendicular to the plural rows. Along each of the plural rows, light emitting elements 2 and 3 are arranged at equal intervals so that a unit comprised of two red light emitting elements 2 and one blue light emitting element 1 repeatedly occurs along each row. Along each of the plural columns, plural red light emitting elements 2 or plural blue light emitting elements 3 are arranged at equal intervals. More specifically, in the arrangement as illustrated in FIG. 2 (a), three red light emitting elements 2 or three blue light emitting elements 3 are arranged at equal intervals along each column. In this arrangement, six red light emitting elements 2 are arranged in two adjacent columns to form a unit 2a, and three blue light emitting elements 3 are arranged in one row to form a unit 3a. The unit 2a of red light emitting elements 2 and the unit 3a of blue light emitting elements 3 are alternately arranged in the longitudinal direction of the light irradiation part 11a.

In the arrangement of light emitting elements 2 and 3 in the light irradiation part 11b as illustrated in FIG. 2 (b), these light emitting elements 2 and 3 are uniformly distributed to form plural rows each extending in parallel in the longitudinal direction of the light irradiation part 11b, and form plural columns each extending in parallel in the direction perpendicular to the plural rows. Along each of the plural rows, light emitting elements 2 and 3 are arranged at equal intervals so that a unit comprised of two red light emitting elements 2 and one blue light emitting element 1 repeatedly occurs along each row similarly to in FIG. 2 (a). The irradiation part 11b as illustrated in FIG. 2 (b) includes three kinds of columns, which are comprised of (i) two red light emitting elements 2 and one blue light emitting element 1 sandwiched between the two red light emitting elements, (ii) two blue light emitting elements 3 and one red light emitting element 2 sandwiched between the two blue light emitting elements 3, and (iii) three red emitting elements 2, respectively. The three kinds of columns alternately occur in the longitudinal direction of the irradiation part 11b.

In the arrangement of light emitting elements 2 and 3 in the light irradiation part 11c as illustrated in FIG. 2 (c), plural light emitting elements 2 and 3 are uniformly distributed to form three rows each extending in parallel in the longitudinal direction of the light irradiation part 11c, that is, red light emitting elements 2 form two rows and blue light emitting elements form a single row, all of the rows extending in the longitudinal direction so that the single row of blue light emitting elements 3 is sandwiched between the two rows of red light emitting elements 2 in the light irradiation part 11c. Light emitting elements 2 or 3 in each row are arranged at equal intervals. In the arrangement illustrated in FIG. 2 (c), the blue light emitting elements 3 are arranged in a single row so that the center between two adjacent blue light emitting elements 3 is located approximately on a straight line connecting the center of two adjacent red light emitting elements 2 in one row to the center of two adjacent red light emitting elements 2 in another row.

In the arrangement of light emitting elements 2 and 3 in the light irradiation part 11d as illustrated in FIG. 2 (d), plural light emitting elements 2 and 3 are uniformly distributed to form three rows each extending in parallel in the longitudinal direction of the light irradiation part 11d so that a unit comprised of two red light emitting elements 2 and one blue light emitting element 3 repeatedly occurs in each row extending in the longitudinally extending direction, similarly to the light irradiation part 11a in FIG. 1 (a). Light emitting elements 2 and 3 in each row are arranged at equal intervals.

In the arrangement illustrated in FIG. 2 (d), the light emitting elements 2 and 3 occurring in the central row sandwiched between two rows are arranged so that the center between two adjacent light emitting elements is located approximately on a straight line connecting the center of two adjacent light emitting elements in one row to the center of two adjacent light emitting elements in another row. Each column comprised of three red light emitting elements 2 or three blue light emitting elements 3 appears inclined from the direction perpendicular to the longitudinal direction.

The light irradiation part of the illumination lamp facility as used in the present invention preferably has a mixed light emitting package such that red light emitting elements and blue light emitting elements are arranged in a single light emitting package. The mixed light emitting package preferably has a function such that the red light emitting elements and the blue light emitting elements are capable of being independently controlled.

The ratio of the light emission intensity of red light to the light emission intensity of blue light in the mixed light emitting package is preferably at least 1:1, more preferably in the range of 2:1 to 9:1, and especially preferably in the range of 2:1 to 5:1. By providing the light irradiation part with such mixed light emitting package, the red light emitting elements and the blue light emitting elements can be arranged with enhanced density in the light irradiation part.

Conventional red light emitting elements 2 and blue light emitting elements 3 can be used. For example, light emitting diode (LED) in which the desired wavelength can be easily selected and light energy within the effective wavelength region occupies a predominant part can be used. Laser diode (LD) and a electroluminescent (EL) element can also be used. The EL element used may be either an organic EL element or inorganic EL element.

Red light emitted from the red light emitting elements 2 has a wavelength in the range of 570 nm to 730 nm. Preferably the red light has a center emission wavelength within the range of 645 nm to 680 nm, and a wavelength in the range of the center emission wavelength ±50 nm, more preferably the center emission wavelength ±30 nm, and especially preferably the center emission wavelength ±10 nm.

Blue light emitted from the blue light emitting elements 3 has a wavelength in the range of 400 nm to 515 nm. Preferably the red light has a center emission wavelength within the range of 410 nm to 510 nm, and a wavelength in the range of the center emission wavelength 450±30 nm, more preferably the center emission wavelength 450±20 nm, and especially preferably the center emission wavelength 450±10 nm.

The red light irradiated to a plant at the red light irradiating step (A) may include a minor proportion of lights other than red light, for example, blue light, provided that the total irradiated light exhibits a red light emission intensity ratio of at least 60%. According to the research of the present inventors, enhancement of plant growth at the red light irradiation step (A) can be observed when the total irradiated light exhibits a blue light emission intensity ratio of up to approximately 30%. The total irradiated light should preferably exhibit a blue light emission intensity ratio of up to approximately 20%, and most preferably zero. An example of the light irradiated to a plant at the red light irradiating step (A) exhibits a red light emission intensity ratio of 60%, a far-infrared light emission intensity ratio of 20% and a blue light emission intensity ratio of 20%. Most preferable example of the light irradiated at the red light irradiating step (A) exhibits a red light emission intensity ratio of 100%.

The blue light irradiated to a plant at the blue light irradiating step (B) may include a minor proportion of lights other than blue light, for example, red light, provided that the total irradiated light exhibits a blue light emission intensity ratio of at least 60%. According to the research of the present inventors, enhancement of plant growth at the blue light irradiation step (B) can be observed when the total irradiated light exhibits a red light emission intensity ratio of up to approximately 30%. The total irradiated light should preferably exhibit a red light emission intensity ratio of up to approximately 20%, and most preferably zero. An example of the light irradiated to a plant at the blue light irradiating step (B) exhibits a blue light emission intensity ratio of 60%, a far-infrared light emission intensity ratio of 20% and a red light emission intensity ratio of 20%. Most preferable example of the light irradiated at the blue light irradiating step (B) exhibits a blue light emission intensity ratio of 100%.

By the term "light emission intensity ratio" as used in the specification, we mean those which are expressed by photosynthetic photon flux density (PPFD; in $\mu mol/m^2 s$).

The red light and the blue light, irradiated from the light irradiation part 11, preferably exhibit a photosynthetic photon flux density in the range of approximately 1 to 1000 $\mu mol/m^2 s$, more preferably approximately 10 to 500 $\mu mol/m^2 s$ and especially preferably approximately 50 to 250 $\mu mol/m^2 s$.

The light emission intensity ratios of individual red light emitting elements and individual blue light emitting elements are not particularly limited, provided that the total red light emission intensity ratio of plural red light emitting elements and the total blue light emission intensity ratio of plural blue light emitting elements are within the above-mentioned range.

Illumination lamp facilities as preferably used for the plant cultivation are equipped with a control part. Emission intensities of red light and blue light, emitted from the irradiation part 11, can be controlled by varying the current value, applied to red light emitting elements 2 and blue light emitting elements 3, by the control part. Thus the ratio of the emission intensity of red light to the emission intensity of blue light can be adequately varied depending upon the particular plant.

The plant cultivating illumination lamp 1 as illustrated in FIG. 1 is provided with a pair of electrodes 41 and 42 for red light emitting elements 2 and a pair of electrodes 43 and 44 for blue light emitting elements 3. The plural red light emitting elements 2 are electrically connected by wires (not shown) to the electrodes 41 and 42. The plural blue light emitting elements 3 are electrically connected by wires (not shown) to the electrodes 43 and 44.

The control part equipped in the illumination lamp facility 1 has a function of independently turning on and off the red light emitting elements 2 and the blue light emitting elements 3 by supplying electric current, respectively, via the electrodes 41 and 42 to the red light emitting elements 2 and via electrodes 43 and 44 to the blue light emitting elements 3.

The control part can be provided with a lamp controller (i.e., light emission intensity-controlling means), which can turn on and off the red light emitting elements 2 and the blue light emitting elements 3 so that the red light and the blue light are irradiated alternately or concurrently, and for a desired period of time. Thus, the light emission intensity ratio of red light to blue light, irradiated from the light irradiation part 11, can be controlled so as to achieve the desired growth of plants.

The lamp controller used includes, for example, one type which can vary the light emission intensities of the red light emitting elements and the blue light emitting elements 3 by supplying different electric currents to a part or all of the red light emitting elements 2 and/or a part or all of the blue light emitting elements 3, thereby controlling the total emission intensity ratio of red light to blue light, irradiated from the light irradiation part 11; and another type which varies the light emission intensities of the red light emitting elements and the blue light emitting elements 3 by supplying an electric current only to a part of the red light emitting elements 2 and/or a part of the blue light emitting elements 3 to turn on a limited number of light emitting elements, thereby controlling the total emission intensity ratio of red light to blue light, irradiated from the light irradiation part 11.

In the plant cultivation lamp 1, as specifically disclosed in FIG. 1, provided with a light irradiation part 11 having the same number of red light emitting elements and blue light emitting elements, and with a lamp controller, the same electric current can be supplied to all of the red light emitting elements 2 and all of the blue light emitting elements 3, whereby red light and blue light which have the same light emission intensity are irradiated from the light irradiation part 11.

Alternatively, a plant cultivation lamp 1 which is provided with a light irradiation part having the same number of red light emitting elements and blue light emitting elements, but is not provided with a lamp controller can be used in the case when the same electric current is supplied to all of the red light emitting elements 2 and all of the blue light emitting elements 3.

As another operation of the plant cultivation lamp 1, as illustrated in FIG. 1, provided with a light irradiation part having the same number of red light emitting elements and blue light emitting elements, and with a lamp controller, different currents can be supplied to the red light emitting elements 2 and the blue light emitting elements 3 so that the light irradiation part 11 irradiates light with an emission intensity ratio of red light to blue light being 2:1.

In the plant cultivation lamp provided with the light irradiation part 11a, 11b, 11c or 11d, as specifically disclosed in FIG. 2, which has twice as many red light emitting elements as blue light emitting elements, and with a lamp controller, the same current can be supplied to all of the red light emitting elements 2 and all of the blue light emitting elements 3 whereby the light irradiation part 11 irradiates light with an emission intensity ratio of red light to blue light being 2:1.

Alternatively, a plant cultivation lamp which is provided with a light irradiation part having twice as many red light emitting elements 2 as blue light emitting elements 3, but is not provided with a lamp controller, can be used in the case when the same electric current is supplied to all of the red light emitting elements 2 and all of the blue light emitting elements 3 whereby the light irradiation part 11 irradiates light with an emission intensity ratio of red light to blue light being 2:1.

As another operation of the plant cultivation lamp 1 provided with the light irradiation part 11a, 11b, 11c or 11d, as specifically disclosed in FIG. 2, which has twice as many red light emitting elements as blue light emitting elements, and with a lamp controller, twice current as large can be supplied to all of the red light emitting elements 2 as to all of the blue light emitting elements 3 whereby the light irradiation part 11 irradiates light with an emission intensity ratio of red light to blue light being 4:1 (red light/blue light).

The emission intensity ratio of red light to blue light, which are irradiated from the light irradiation part 11, is preferably at least 1:1, more preferably in the range of 2:1 to 9:1, and especially preferably in the range of 2:1 to 5:1, as mentioned above. In the case when the emission intensity ratio of red light to blue light is in this range, a highly enhanced plant growth can be attained by the sufficiently enhanced red light emission intensity as compared with the blue light emission intensity. When the emission intensity ratio of red light to blue light is smaller than the above-specified range, the desired high plant growth-enhancing effect is often difficult to attain. In contrast, when the emission intensity ratio of red light to blue light is larger than the above-specified range, the desired high plant growth-enhancing effect is also often difficult to attain and undesirable growth such as spindly growth sometimes occurs.

The provision of the light irradiation part having the red light emitting elements 2 and blue light emitting elements 3 is also advantageous as compared with the conventional illumination lamp facility having red light emitting means and blue light emitting means which are separately arranged, because the light emitting means can be easily and steadily arranged in the illumination lamp facility 1 and undesirable deviation of the irradiation directions of red light and blue light can be minimized.

The light irradiation part 11 as illustrated in FIG. 1 has a rectangular shape in a plan view, therefore, the illumination lamp facility 1 can be easily set in the position in which a conventional illumination facility such as straight tube fluorescent lamp is set.

The illumination lamp facility is preferably provided with a converter, built in the lamp, of converting alternating current to direct current for LED because of ease in setting and effective utilization of space. The terminal on one side and the terminal on the other side are preferably utilized separately for the red light emission and blue light emission in view of arrangement of electrical sources built therein and dispersion in generation of heat.

Further the illumination lamp facility is preferably provided with a dimmer for controlling LED in plural lamps and desirably adjusting the light emission intensity ratio.

Plant Cultivation Method

The method of cultivating a plant according to the present invention will now be explained specifically and more in detail on an embodiment using the illumination lamp 1 as illustrated in FIG. 1.

The plant cultivation method of the present invention comprises a step (A) of irradiating a plant with a red light (which is hereinafter referred to as "red light-irradiation step (A)" when appropriate) and a step (B) of irradiating a plant with a blue light (which is hereinafter referred to as "blue light irradiation step (B)" when appropriate), wherein the red light-irradiation step (A) and the blue light irradiation step (B) are independently carried out for a predetermined period of time.

Preferably, the red light-irradiation step (A) and the blue light irradiation step (B) are alternately and repeatedly carried out over a period of at least three hours for each irradiation time.

By the term "independently" as used herein, we mean that the red light-irradiation step (A) and the blue light irradiation step (B) exist separately in the course of plant cultivation.

By the term "predetermined period of time" as used herein, we mean an optional length of time within the course of plant cultivation. The maximum length of the predetermined period of time equals to the entire time length of the course of plant cultivation. The minimum length thereof can be voluntarily set provided that the desired plant growth-enhancing effect can be attained. The predetermined period of time can be expressed in unit of hour, day or minute depending upon the particular length of time.

Each of the red light irradiation step (A) and the blue light irradiation step (B) is carried out independently at least once, preferably at least two times, for the predetermined period of time. In the case when the red light irradiation step (A) and the blue light irradiation step (B) are carried out dividedly in two times or more, time length of each operation of the red light irradiation step (A) and time length of each operation of the blue light irradiation step (B) are preferably at least one hour, for example, 1 to 48 hours, and more preferably at least 3 hours, for example, 3 to 24 hours.

The red light irradiation step (A) and the blue light irradiation step (B) can be carried out either alternately and continuously, or intermittently with interposition of an operation of concurrently irradiating plant with red light and blue light between each operation of the red light irradiation step (A) and each operation of the blue light irradiation step (B), or with pause of irradiation between each operation of the red light irradiation step (A) and each operation of the blue light irradiation step (B).

Transfer between operation of red light irradiation step (A) and operation of red light irradiation step (A) can be conducted either instantaneously or over a certain length of time. The transfer may be conducted in stages. During the transfer, operation of red light irradiation step (A) and operation of red light irradiation step (A) may overlap with each other, or a pause of irradiation may intervene between operation of red light irradiation step (A) and operation of red light irradiation step (A).

Alternate flashing of red light irradiation and blue light irradiation by quickly repeating light flashing with a high frequency such as 1 Hz or higher is excluded from the light irradiation procedure adopted for independently carrying out the red light irradiation step (A) and the blue light irradiation step (B) for a predetermined period of time in the plant cultivation method of the present invention.

It is presumed that the mechanism of growth occurring due to light irradiation in the plant cultivation method of the present invention is different from the mechanism of growth occurring due to the alternate flashing of red light irradiation and blue light irradiation by quickly repeating light flashing with a high frequency such as 1 Hz or higher. In other words, in the case when operation of light irradiation is quickly repeated, the plant growth effect brought about by the flashed light irradiation would vary greatly depending upon each time length of light irradiation.

In the plant cultivation method of the present invention, each operation for the red light-irradiation step (A) and each operation for the blue light irradiation step (B) are carried out for a period of time sufficient for allowing the photosynthesis reaction and related reactions to occur in connection with environmental changes to an extent such that the desired plant growth is achieved.

In contrast, in the alternate flashing of red light irradiation and blue light irradiation by quickly repeating light flashing with a high frequency such as 1 Hz or higher, the photosynthesis reaction and related reactions do not occur to the desired extent. This is because each flashing of red light irradiation and blue light irradiation occurs for a very short length of time which is insufficient for achieving the plant growth effect. The plant growth effect achieved by the alternate flashing is similar to that achieved by the operation of concurrently irradiating plant with red light and blue light.

The plant cultivation method of the present invention can be adopted for any period of time within the entire course of plant cultivation spanning from the time immediately after the germination of seeds or immediately after the plantation of seedlings to the time of harvest of grown plants.

In the plant cultivation method of the present invention, the red light-irradiation step (A) and the blue light irradiation step (B) are independently carried out under cultivation conditions such that the humidity in a cultivation atmosphere at the red light irradiation step (A) is higher than that at the blue light irradiation step (B).

More specifically the humidity in a cultivation atmosphere at the red light irradiation step (A) is preferably maintained in the range of 60% to 90%, more preferably in the range of 65% to 80%, and the humidity in a cultivation atmosphere at the blue light irradiation step (B) is preferably maintained in the range of 40% to 60%, more preferably in the range of 45% to 55%.

The difference between the humidity in a cultivation atmosphere at the red light irradiation step (A) and the humidity in a cultivation atmosphere at the blue light irradiation step (B) is preferably in the range of 10% to 30%.

With regard to the temperature, the temperature in a cultivation atmosphere at the red light irradiation step (A) is maintained preferably in the range of 18° C. to 25° C., and the temperature in a cultivation atmosphere at the blue light irradiation step (B) is also preferably maintained in the range of 18° C. to 25° C.

It is preferable that the cultivation atmosphere at the red light irradiation step (A) is maintained at a humidity higher than the humidity of the cultivation atmosphere at the blue light irradiation step (B) while an air stream is allowed to flow in the cultivation atmosphere at a flow rate in the range of 0.1 m/sec to 0.5 m/sec, more preferably 0.2 m/sec to 0.4 m/sec, at the red light irradiation step (A), and at a flow rate in the range of 0.3 m/sec to 1 m/sec, more preferably 0.4 m/sec to 0.6 m/sec, at the blue light irradiation step (B). By allowing an air stream to flow at the above-mentioned flow rate, the photosynthesis process of chlorophyll and related reaction processes, transpiration, and perspiration proceed more smoothly.

Preferably the flow rate of an air stream at the red light irradiation step (A) is at least 0.1 m/sec larger than the flow rate of an air stream at the blue light irradiation step (B). The difference between the flow rate of an air stream at the red light irradiation step (A) and the flow rate of an air stream at the blue light irradiation step (B) is more preferably in the range of 0.2 m/sec to 0.3 m/sec. By controlling the difference in the flow rate of an air stream between the red light irradiation step (A) and the blue light irradiation step (B) in the above-specified ranges, desired temperature and humidity spread adequately and uniformly over the plants, and consequently the photosynthesis process of chlorophyll and other related reaction processes proceed far more smoothly.

The procedure by which the cultivation atmosphere with the desired temperature and humidity is realized is not particularly limited, and a conventional procedure can be adopted. A preferable procedure comprises supplying an air stream having the desired temperature and humidity at an appropriate flow rate by using an air conditioner with an enhanced controlling capability. The flow rate of an air stream can be controlled by varying the number of rotation of an air-blowing fan or a damper opening at an air outlet of an air conditioner.

The plants to be cultivated by the method of the present invention are not particularly limited, and this term means plants in a broad sense which include leaf plants, root plants, fruit plants, pluses, grains, seeds, algae, house plants and mosses.

The plant cultivation method of the present invention should not be construed to be limited to the modes described above.

The illumination lamp facility described above is equipped with a lamp controlling means for controlling light emission intensity. The plant cultivation can also be carried out using an illumination lamp facility not equipped with the lamp controlling means. This illumination lamp facility is advantageous in that a lamp controlling means and its accessories can be omitted and the cost of equipment production is reduced.

EXAMPLES

Preparation of Plants

In the following examples, reference example and comparative example, leaf lettuce (variety: summer serge) was tested for observing the growth state.

Six seeds of leaf lettuce were sown at equal intervals in each test group on a peat van culture medium, and irradiated with fluorescent light for 12 hours of light per day to be thereby germinated. The seeds were placed under the same irradiation conditions over a period of three days spanning from seeding to germination. Thereafter seedlings were raised under irradiation with fluorescent light to give leaf lettuces for test.

Example 1

The raised seedlings of test leaf lettuces were placed in an environment control room wherein carbon dioxide concentration was maintained at 1000 ppm.

An illumination lamp for plant cultivation used had a light emitting part provided with 180 red light emitting elements and 60 blue light emitting elements. Each red light emitting element was comprised of an LED emitting red light with a central wavelength of 660 nm and a wavelength region of 640-680 nm. Each blue light emitting element was comprised of an LED emitting blue light with a central wavelength of 450 nm and a wavelength region of 430-470 nm. The illumination lamp further had a control part for controlling the light emitting part so that the red light emitting elements and blue light emitting elements are independently turned on and off.

The red light emitting elements exhibited a total emission intensity, i.e., a total photosynthetic photon flux density (PPFD), of 150 $\mu mol/m^2 \cdot s$. The blue light emitting elements exhibited a total emission intensity, i.e., a total photosynthetic photon flux density (PPFD), of 50 $\mu mol/m^2 \cdot s$. Thus the total emission intensity ratio of red light to blue light was 3:1.

The red light irradiation step and the blue light irradiation step were alternately and repeatedly carried out for 12 hours for each irradiation time per day, i.e., each light irradiation step was carried out separately and continuously over a period of 12 hours per day. There was no time for which the light irradiation was ceased.

At the red light irradiation step, the temperature and humidity in the environment control room were maintained at 20° C. and 75%, respectively. Under such temperature-humidity conditions, an air stream was circulated at a flow rate of 0.3 m/sec in the environment control room. At the blue light irradiation step, the temperature and humidity in the environment control room were maintained at 20° C. and 50%, respectively. Under such temperature-humidity conditions, an air stream was circulated at a flow rate of 0.6 m/sec in the environment control room.

A combination of the continuous irradiation of red light over a period of 12 hours per day with the continuous irradiation of blue light over a period of 12 hours per day was repeated for 24 days.

When 24 days elapsed, the light irradiation was stopped and grown leaf lettuces were harvested. Leaves were collected from rolled lettuces, and, fresh weight (g) of above-ground part of the lettuces and the total content (mg) of ascorbic acid per 100 g of the lettuces were measured. The measurement results are shown in Table 1. The fresh weight and the total content of ascorbic acid are expressed by relative index as the values in Example 1 being 100.

TABLE 1

| | Examples, Comparative Examples | | | |
|---|---|---|---|---|
| | Ex. 1 | Ex. 2 | Ref. Ex. 1 | Co. Ex. 1* |
| Red light irradiation | | | | |
| Temperature (° C.) | 20 | 20 | 20 | 20 |
| Humidity (%) | 75 | 75 | 75 | 75 |
| Flow rate of air stream (m/sec) | 0.3 | 0.5 | 0.3 | 0.3 |
| Blue light irradiation | | | | |
| Temperature (° C.) | 20 | 20 | 20 | 20 |
| Humidity (%) | 50 | 50 | 75 | 75 |
| Flow rate of air stream (m/sec) | 0.6 | 0.5 | 0.3 | 0.3 |
| Cultivation results | | | | |
| Total ascorbic acid content | 100 | 98 | 88 | 88 |
| Fresh weight of above-ground part | 100 | 97 | 103 | 60 |

Note;
*In Comparative Example 1, red light and blue light were concurrently irradiated

Example 2

By the same procedures as described in Example 1, leaf lettuces were cultivated except that an air stream was circulated at a flow rate of 0.5 m/sec at both of the red light irradiation step and the blue light irradiation step over the entire cultivation process. All other cultivation conditions remained the same as in Example 1. The cultivation results are shown in Table 1. The cultivation results are expressed by relative indexes as the values in Example 1 being 100.

Reference Example 1

By the same procedures as described in Example 1, leaf lettuces were cultivated except that the temperature and humidity in the environment control room were maintained at 20° C. and 75% respectively. An air stream was circulated at a flow rate of 0.3 m/sec. The temperature, humidity and flow rate of air stream were kept constant at both of the red light irradiation step and the blue light irradiation step over the entire cultivation process. All other cultivation conditions remained the same as in Example 1.

The cultivation results are shown in Table 1. The cultivation results are expressed by relative indexes as the values in Example 1 being 100.

Comparative Example 1

By the same procedures as described in Example 1, leaf lettuces were cultivated except that the red light irradiation step and the red light irradiation step were concurrently and continuously carried out for 12 hours per day, and the lamp was left put out for 12 hours per day. The concurrent irradiation of red light and blue light, and the lamp leaving put out were repeated for 24 days. The temperature and humidity in the environment control room were maintained at 20° C. and 75% respectively. An air stream was circulated at a flow rate of 0.3 m/sec. The temperature, humidity and flow rate of air stream were kept constant at both of the red light irradiation step and the blue light irradiation step over the entire cultivation process. All other cultivation conditions remained the same as in Example 1.

The cultivation results are shown in Table 1. The cultivation results are expressed by relative indexes as the values in Example 1 being 100.

As seen from the cultivation results in Table 1, when the humidity at the red light irradiation step is higher than that at the red light irradiation step according to the present invention (Examples 1 and 2), the fresh weight of above-ground part of the lettuces and the total content of ascorbic acid are approximately the same as or only slightly smaller than those in the case when the humidity at the red light irradiation step is the same as that at the red light irradiation step (Reference Example 1), but, the total ascorbic acid contents in Examples 1 and 2 are larger than those in Comparative Example 1.

When the red light irradiation and the blue light irradiation are concurrently carried out (Comparative Example 1), the plant growth is slow and the total ascorbic acid content is low, therefore, the fresh weight of the above-ground part is very small and thus the productivity is poor. The total ascorbic acid content is low.

According to the cultivation method of the present invention, although the plant growth is enhanced, plants having a high ascorbic acid content can be produced.

The invention claimed is:

1. A method of cultivating a plant comprising a step (A) of irradiating a plant with a red light and a step (B) of irradiating the plant with a blue light, wherein the red light irradiating step (A) and the blue light irradiating step (B) are independently carried out for at least one predetermined period of time under cultivation conditions such that the humidity in a cultivation atmosphere at the red light irradiating step (A) is higher than that at the blue light irradiating step (B).

2. The method of cultivating a plant according to claim 1, wherein the humidity in the cultivation atmosphere at the red light irradiating step (A) is in the range of 60% to 90% and the humidity in the cultivation atmosphere at the blue light irradiating step (B) is in a range of 40% to 60%.

3. The method of cultivating a plant according to claim 2, wherein the temperature in the cultivation atmosphere at the red light irradiating step (A) is in a range of 18° C. to 25° C. and the temperature in the cultivation atmosphere at the blue light irradiating step (B) is in the range of 18° C. to 25° C.

4. The method of cultivating a plant according to claim 1, wherein the humidity of the cultivation atmosphere at the red light irradiating step (A) is maintained higher than the humidity of the cultivation atmosphere at the blue light irradiating step (B), while an air stream is allowed to flow in the cultivation atmosphere at a flow rate in a range of 0.1 meters/second (m/sec) to 0.5 m/sec at the red light irradiating step (A) and at a flow rate in a range of 0.3 m/sec to 1 m/sec at the blue light irradiating step (B).

5. The method of cultivating a plant according to claim 1, wherein the red light irradiating step (A) and the blue light irradiating step (B) are alternately and repeatedly carried out over a period of at least one hour for each at least one predetermined period of time.

6. The method of cultivating a plant according to claim 1, wherein the red light irradiating step (A) and the blue light irradiating step (B) are carried out using an illumination lamp facility having red light emitting elements and blue light emitting elements, which are capable of being independently operated, and the red light emitting elements and the blue light emitting elements exhibit a light emission intensity ratio of red light to blue light of at least 1:1 as expressed by a ratio of photosynthetic photon flux density of red light to blue light.

7. The method of cultivating a plant according to claim 1, wherein the red light irradiating step (A) and the blue light irradiating step (B) are carried out using an illumination lamp facility having red light emitting elements and blue light emitting elements, which are capable of being independently operated, and the red light emitting elements and the blue light emitting elements exhibit a light emission intensity ratio of red light to blue light in the range of 2:1 to 9:1 as expressed by a ratio of photosynthetic photon flux density of red light to blue light.

* * * * *